United States Patent Office

Plant Pat. 2,500
Patented Apr. 27, 1965

2,500
ROSE PLANT

Paul Croix, Bourg-Argental, Loire, France, assignor to The Conard-Pyle Company, West Grove, Pa., a corporation of Pennsylvania

Filed Feb. 24, 1964, Ser. No. 347,102
Claims priority, application France, Mar. 22, 1963, 8,653/63
1 Claim. (Cl. Plt.—20)

The present invention relates to a new and distinct variety of rose plant of the hybrid tea class, which was originated by me by crossing an unnamed and unpatented seedling derived from crossing two unnamed and unpatented varieties resulting from crosses of the variety known in the United States as "Independence" (U.S. Plant Patent No. 1,036) with the variety known as "Geranium" (unpatented), with another unnamed and unpatented seedling derived from a cross of the variety named "Sunder" (unpatented) × "Baccara" (U.S. Plant Patent No. 1,367).

The primary objective of this breeding was to produce a new and improved rose variety which bears flowers of a new color, in addition to being fuller, more copious, with the flowers having good petalage and good longevity, in addition to having good resistance to diseases. These objectives were fully achieved, along with other desirable improvements, as evidenced by the following unique combination of characteristics which are outstanding in the new variety and which distinguish it from its parents, as well as from all other varieties of which I am aware:

(1) A moderately tall, erect and freely branched habit of growth;

(2) Abundant, glossy green foliage;

(3) Buds of pointed ovoid form;

(4) A habit of normally bearing flowers singly to the stem;

(5) Well formed flowers which are high centered on opening, but which become cupped at maturity;

(6) Good flower petalage normally ranging from 45 to 50 petals;

(7) A distinctive and atractive vermilion general color tonality of the flowers; and (8) A slight tea fragrance of the flowers.

Asexual reproduction of my new variety by budding, as performed in France and at West Grove, Pennsylvania, U.S.A., shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with the Horticultural Colour Chart of the Royal Horticultural Society, except where general color terms of ordinary dictionary significance are obvious:

Type: Hardy; bush; outdoor; seedling; for garden decoration.

Class: Hybrid tea.

Breeding: Seedling.

*Seed parent.*—An unnamed seedling derived from a cross of two unnamed varieties resulting from a cross of "Independence" × "Geranium."

*Pollen parent.*—An unnamed seedling derived from a cross of "Sunder" × "Baccara."

Propagation: Holds its distinguishing characteristics through succeeding propagations by budding.

*Flower*

Locality where grown and observed: West Grove, Pennsylvania, U.S.A.

Flowers borne: Usually singly, but sometimes several to a stem; on stems of normal strength, ranging from medium length to long.

Quantity of bloom: From moderate to free, outdoors.

Continuity: Continuous.

Fragrance: Slight. Nature—tea.

Bud:

*Peduncle.*—Long; medium caliper; erect; stiff; smooth; with few red-brown hairs. Color—green overlaid bronze.

*Before calyx breaks.* — Size — medium. Form—pointed ovoid; with a conspicuous neck; with foliaceous appendages on the surface of the bud; with medium thick much-cut bristle-like foliaceous parts extending beyond the tip of the bud equal to one-half or more of its length.

*As calyx breaks.*—Color—Signal Red, Plate 719.

*As first petal opens.*—Size—medium. Form—from short to medium length; ovoid. Color: outside—Geranium Lake, Plate 20/1, occasionally spotted and blotched with blackish purple; inside—Vermilion, Plate 18, occasionally with a greenish stripe running from point of attachment toward the apex.

*Opening.*—Opens up well.

Bloom:

*Size (when fully open).*—Large; from 4¼ inches to 5 inches.

*Petal.*—Double; from 45 to 50 petals; arranged regularly.

*Form.*—High-centered at first, but becoming cupped; petals at first being loosely rolled outward and remaining loosely rolled outward at maturity.

Petals:

*Texture.*—Medium thickness; leathery.

*Appearance.*—Inside—velvety. Outside—satiny.

*Shape.*—Outer petals—round; with one or two notches. Intermediate—round; with one or two notches. Inner petals—undulate; with variable number of notches.

This description of a newly opened flower was made from a rose grown outdoors during the month of October at West Grove, Pennsylvania, U.S.A.:

*Color.*—Outer petal: outside surface—Rose Opal, Plate 022/1; inside surface—Scarlet, Plate 19. Intermediate petal: outside surface—Rose Opal, Plate 022/1, becoming Delft Rose, Plate 020/1 over lower half of petal; inside surface—Scarlet, Plate 19. Inner petal: outside surface—Claret Rose, Plate 021/1, occasionally streaked with Magnolia Purple, Plate 030/1; inside surface—Jasper Red, Plate 018 over upper half of petal, with basal half Vermilion, Plate 18/1.

This description was made from a rose that was open for three days outdoors during the month of October at West Grove, Pennsylvania, U.S.A.:

*Color.*—Outer petal: outside surface—Delft Rose, Plate 020, occasionally with irregular purplish spots and streaks; inside surface—Scarlet, Plate 19. Inner petal: outside surface—Carmine Rose, Plate 621/1; inside surface—Scarlet, Plate 19/1, becoming washed with Empire Rose, Plate 0621 toward base of petal.

*General color effect.*—Newly opened flower—between Vermilion, Plate 18 and Vermilion, Plate 18/1. 3-days open—Vermilion, Plate 18, becoming Vermilion, Plate 18/1 toward center of flower.

*Behavior.*—Drop off cleanly; during cold weather Vermilion general color tonality becomes somewhat lighter at maturity.

*Flower longevity.*—On bush in garden—4 days in October. Cut roses grown outdoors and kept at living room temperatures—5 days in October.

*Reproductive organs*

Stamens: Many; arranged regularly about pistils; mixed with petaloids.

Filaments: Many; medium length; most with anthers. Color—yellow gold.

Anthers: Medium size; occasionally an anther fused with a petaloid; open at various times. Color—yellow.

Pollen: Moderate quantity. Color—yellow gold.

Pistils: Many.

Styles: Uneven; medium length; thin; bunched.

Stigma: Color—yellow.

Ovaries: All enclosed in receptacle.

Hips: Medium length; globular; with inconspicuous neck; smooth; walls thick and dry. Color—green.

Sepals: Permanent; moderately long; spear-shaped.

Seeds: Medium number; small.

*Plant*

Foliage:

*Leaves.*—Compound of 5 leaflets; from normal quantity to abundant; moderately large; leathery; glossy.

*Leaflets.*—Shape—oval; with apex acute. Base—obtuse. Margin—simply serrate.

*Color.*—Mature: upper surface—Parsley Green, Plate 00962; under surface—Sage Green, Plate 000861/1. Young: upper surface—near Oxblood Red, Plate 00823; under surface—Oxblood Red, Plate 00823, overlaid with Erythrite Red, Plate 0027.

*Rachis (the supporting stem of the compound leaf).*—Medium size. Upper side — grooved; hairy. Under side—sparsely prickly.

*Stipules.*—Medium length; moderately narrow; with short points turning out at an angle of 45°.

*Disease resistance.*—Comparable to that of the average rose variety grown under the same cultural conditions at West Grove, Pennsylvania, U.S.A.

Growth:

*Habit.*—Bushy; upright; much-branched.

*Growth.*—Free.

*Canes.*—Moderately heavy.

*Main stems.*—Dull. Color—Parsley Green, Plate 00962/2. Prickles—many; color—brown. Hairs—none.

*Branches.* — Dull. Color — Parsley Green, Plate 00962/2, sometimes with a brownish overlay. Prickles—many; color—reddish. Hairs—none.

*New shoots.*—Dull. Color—Maroon, Plate 1030, with greenish undertones. Prickles — many; color—Maroon, Plate 1030. Hairs—none.

I claim:

A new and distinct variety of rose plant of the hybrid tea class, substantially as herein shown and described, characterized particularly as to novelty by the unique combination of a moderately tall, erect and freely branched habit of growth, abundant, glossy green foliage, flower buds of pointed ovoid form, a habit of normally bearing the flowers singly to a stem, said flowers being well formed and being high centered on opening but becoming cupped at maturity, good flower petalage, a distinctive and attractive Vermilion general color tonality of the flowers, and a slight tea fragrance of the flowers.

No references cited.

ABRAHAM G. STONE, *Primary Examiner.*

April 27, 1965 P. CROIX Plant Pat. 2,500
ROSE PLANT
Filed Feb. 24, 1964
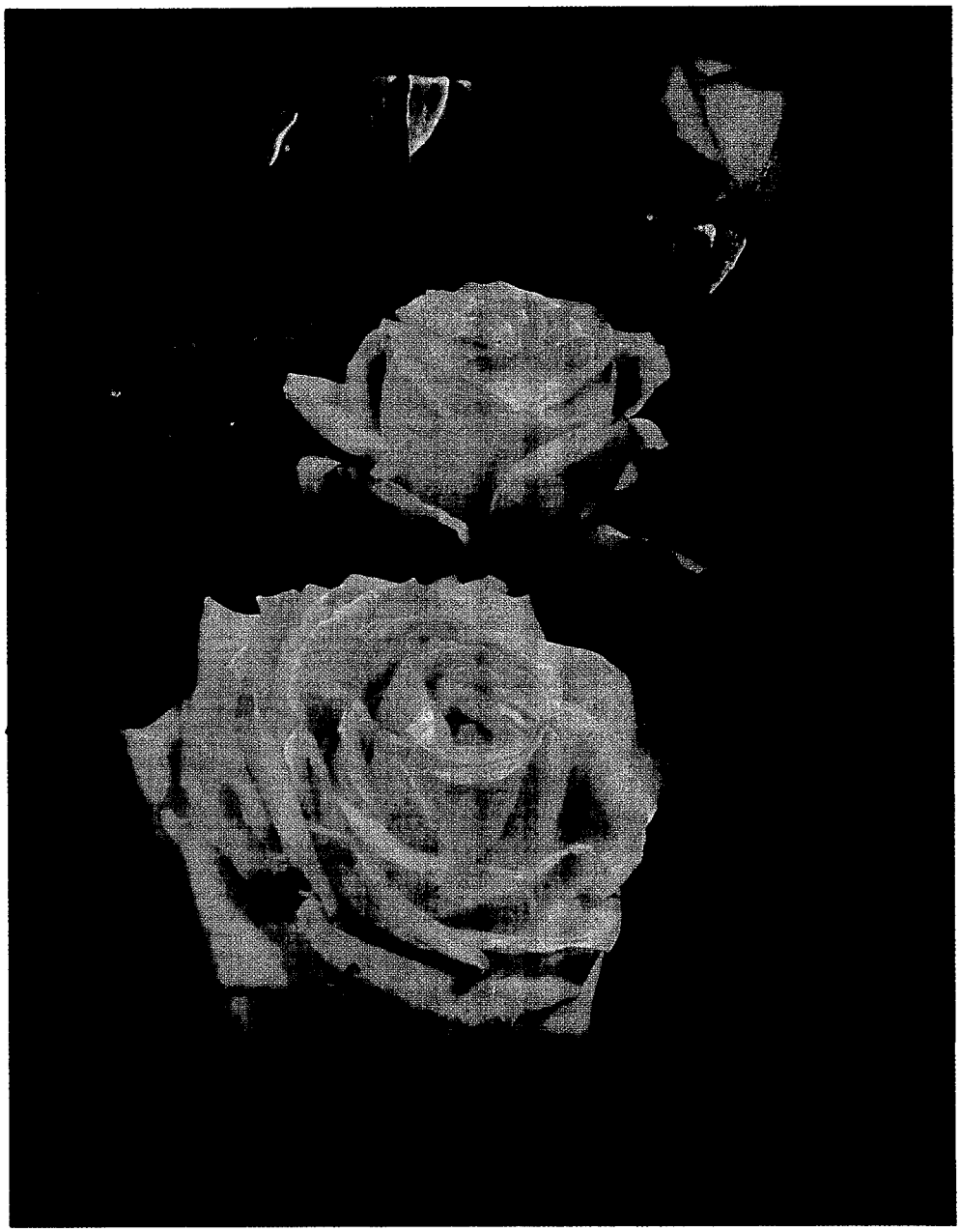
Inventor.
Paul Croix
By: Robb & Robb
Attorneys.